Figure 1:
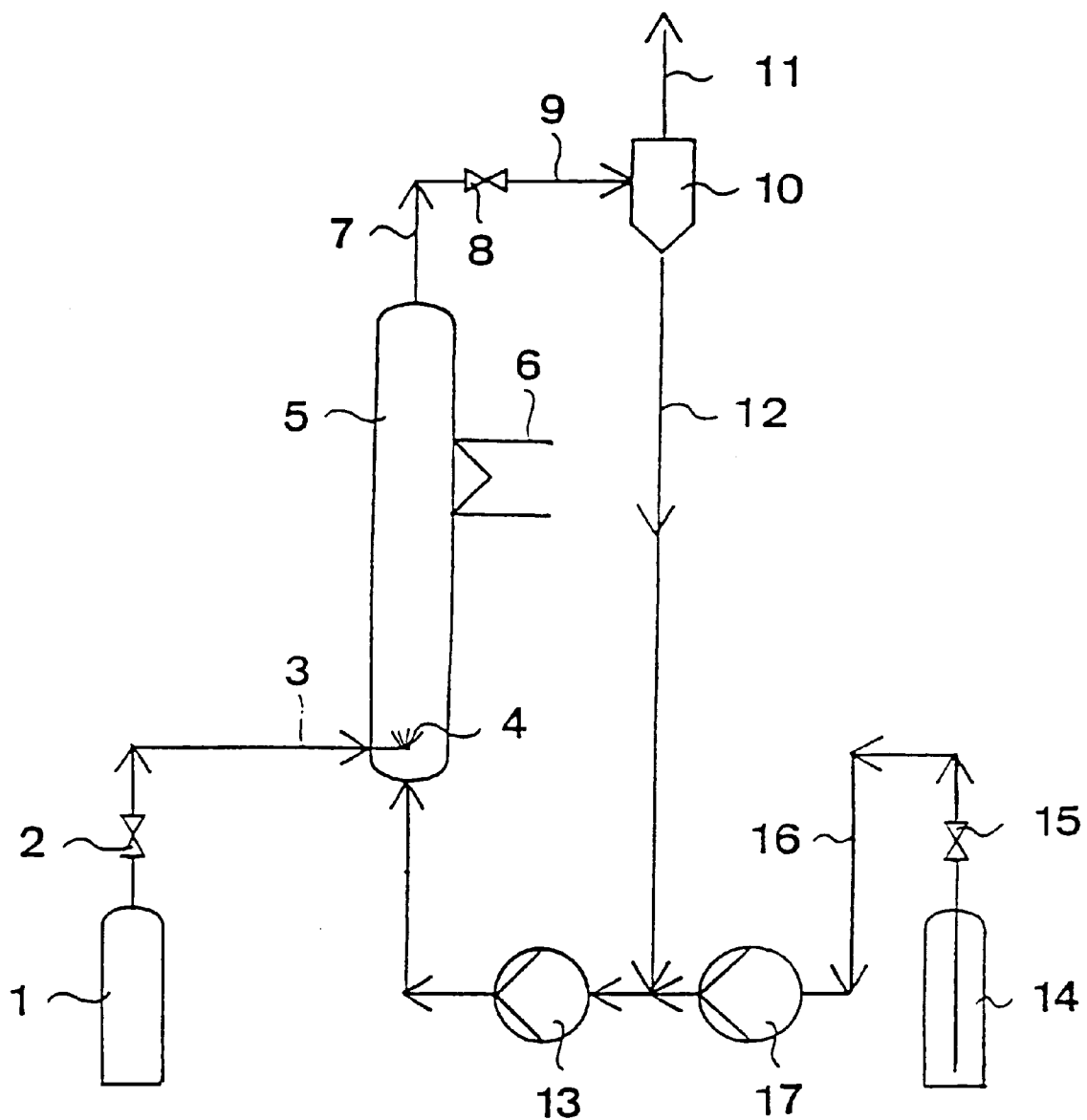

United States Patent [19]

Hopp et al.

[11] Patent Number: 6,118,033

[45] Date of Patent: Sep. 12, 2000

[54] METHOD FOR PREPARING HEPTAFLUOROPROPANE

[75] Inventors: Peter Hopp, Hofheim; Wolf-Dietmar Kaufmann, Krouberg, both of Germany

[73] Assignee: Solvay (Societe Anonyme), Brussels, Belgium

[21] Appl. No.: 09/029,233

[22] PCT Filed: Sep. 17, 1996

[86] PCT No.: PCT/EP96/04095

§ 371 Date: Jun. 10, 1998

§ 102(e) Date: Jun. 10, 1998

[87] PCT Pub. No.: WO97/11042

PCT Pub. Date: Mar. 27, 1997

[30] Foreign Application Priority Data

Sep. 20, 1995 [DE] Germany .......................... 195 34 917

[51] Int. Cl.[7] .................................................... C07C 17/08
[52] U.S. Cl. .......................................... 570/165; 570/164
[58] Field of Search ...................................... 570/164, 165

[56] References Cited

FOREIGN PATENT DOCUMENTS

| 2127732 | 1/1995 | Canada . |
| 0634383 | 1/1995 | European Pat. Off. . |

*Primary Examiner*—Alan Siegel
*Attorney, Agent, or Firm*—Venable

[57] ABSTRACT

The invention relates to the continuous preparation of heptafluoropropane by conversion of hexafluoropropene with HF in the presence of a liquid hydrofluoride of an organonitrogen base corresponding to the formula [B×nHF], in which B represents an organonitrogen base and n represents an integer or a fraction $\leq 4$, during which HF, hexafluoropropene and the hydrofluoride are converted in a first zone at an elevated pressure $p_1$, the resulting heptafluoropropane is then evaporated off and isolated from the liquid reaction mixture, in a second zone under a pressure $p_2 < p_1$, and the remaining liquid reaction mixture is then transferred back into the first zone.

11 Claims, 1 Drawing Sheet

METHOD FOR PREPARING HEPTAFLUOROPROPANE

The invention relates to a process for the continuous preparation of 1,1,1,2,3,3,3-heptafluoropropane (referred to hereinbelow as heptafluoropropane) by conversion of hexafluoropropene with HF in the presence of a liquid hydrofluoride of an organonitrogen base corresponding to the general formula [B×nHF], where n represents an integer or a fraction $\leq 4$ and B represents an organonitrocen base.

Document EP-A-0,634,383 describes a general process for the addition of hydrogen fluoride to haloalkenes corresponding to the general formula $R^1CF=CR^2R^3$ with such a hydrofluoride [B×NHF], preferably [$(CH_3)_3N \times 2.8$ HF] or [$(C_2H_5)_3N \times 2.8$ HF], as catalyst. The tests with hexafluoropropene are described on a laboratory scale, both in terms of batchwise production and continuous production. However, complete conversion is not obtainer in the case of the two embodiment variants. On account of its high price, the residual hexafluoropropene contained in the final heptafluoropropane product must be recovered by an expensive distillation.

The objective was to develop a continuous process or the preparation of heptafluoropropane with complete conversion of the hexafluoropropene.

In the abovementioned document EP-A-0,634,383, Examples 4 and 5 use a bubble column (container for the reaction with liquid hydrogen fluoride catalyst which is fully charged with gas bubbles of the reactants and of the product) for the continuous conversion of hexafluoropropene with HF. The degree of conversion of hexafluoropropene amounts to 98.4 and 99% respectively. Although these values appear to be relatively high, they are not, however, high enough to make the abovementioned distillation treatment redundant.

It has now been found that the degree of conversion of hexafluoropropene can be increased to at least 99.99% by passing the reaction mixture through two zones arranged in series, a higher pressure prevailing in the first zone by comparison with that in the second zone. On account of the virtually quantitative conversion, removal of the unconverted starting material by distillation is not necessary. In addition, the process in accordance with the present invention can be carried out on a large scale without any problems, which is not as easy to do in the case of a bubble column.

The subject of the present invention is a process for the continuous preparation of heptafluoropropane by conversion of hexafluoropropene with HF in the presence of at least one liquid hydrofluoride of an organonitrogen base corresponding to formula (I)

[B×nHF]     (I), in which B represents an organonitrogen base and n represents an integer or a fraction $\leq 4$, characterized in that HF and hexafluoropropene are converted, in a cyclic process, in the presence of a liquid hydrofluoride corresponding to formula (I), in a first zone under a pressure $p_1=1.3$ to 10 bar, in that the liquid reaction mixture is then transferred to a second zone and that it comes under a pressure $p_2<p_1$ therein, in which $p_1-p_2 \geq 0.3$ bar and $p_2 \geq 1$ bar, in that the resulting heptafluoropropane is evaporated and isolated from the liquid reaction mixture, and in that the remaining liquid reaction mixture is then transferred, after addition of hexafluoropropene and HF, back into the first zone.

The reaction temperature in the first zone is preferably 40 to 100° C., in particular 50 to 80° C. Suitable hydrofluorides, that are liquid at these temperatures, corresponding to formula (I) are, for example, [$(CH_3)_3N \times 2.8$ HF], [$(C_2H_5)_3N \times 2.8$ HF] and [$(C_4H_9)_3N \times 2.6$ HF], as well as

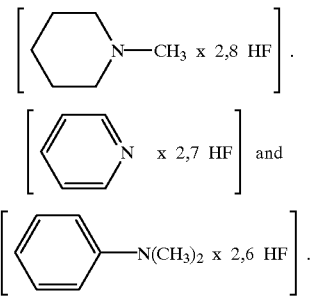

One of the three hydrofluorides mentioned previously is preferably used. However, any of the other hydrofluorides corresponding to formula (I), mentioned in document EP-A-0,634,383, that are liquid at the reaction temperatures chosen, are also suitable. The preparation of the hydrofluorides is also described in document EP-A-0,634,383, to which reference is made explicitly herein. Besides hexafluoropropene, the haloalkenes indicated in that document can be converted in a similiar manner to the present process, during which process they react in a yield about as high as that of hexafluoropropene.

In the first zone, a pressure $p_1=1.3$ to 10 bar is adjusted; preferably $p_1=1.5$ to 5 bar. In the second zone, a pressure $p_2<p_1$ is adjusted, in which $P_2 \geq 1$ bar and the pressure difference $p_1-p_2 \geq 0.3$ bar. Preferably, the pressure difference $p_1-p_2 0.3$ to 2 bar, which can always be adjusted by an appropriate choice of $p_1$ and $p_2$ within the limits indicated.

The heptafluoropropane evaporated off and isolated, or removed by distillation, has a purity of greater than 99% with a yield of greater than 99%.

FIG. 1 is a schematic flow sheet of the process.

In FIG. 1, Hexafluoropropene (HFP) is removed in gaseous form from the storage reservoir (1) and is introduced via the valve (2), the pipe (3) and the gas distribution system (4) (for example filter sinters, sintered filters, nozzle bottoms) into the reactor (5) serving as the first zone, which is heated by means of a heating system (6). The reactor (5) is filled with the liquid hydrofluoride catalyst. The HFP is first dispersed in the catalyst, via the gas distribution system (4), in the form of small bubbles which dissolve rapidly and completely. The presence of gas bubbles is limited to the lower region of the reactor (about ⅕ of the total volume), such that it is not a bubble column (i.e. a reactor fully charged with gas bubbles).

The reaction mixture is conveyed, via the pipe (7), the valve (8) and the pipe (9), to the container (10) serving as the second zone, and from this location, via the pipe (12) and the pump (13), back into the reactor (5). The desired heptafluoropropane product is removed from the container (10) via the pipe (11).

The pressure $P_1$ in the reactor (5) is adjusted by means of the valve (8) (for example a shut-off member or a lift valve), and in the container (10) the pressure $p_2<p_1$.

The HF is removed in liquid form from the storage reservoir (14) and is introduced via the valve (15), the pipe (16) and the pump (17) into the pipe (12) and is then conveyed, via the pump (13), together with the catalyst pumped by this pump, into the reactor (5).

EXAMPLE 1

The process was performed in the apparatus described above. The reactor (5) consisted of V4A-type steel (length=

3000 mm, diameter=134.5 mm). Tri-n-butylammonium trihydrofluoride (65 kg) was used as catalyst. The temperature in the reactor (5) was 65° C. The pressure in the reactor (5) was $p_1$=1.8 bar and in the container (10) $P_2$=1.0 bar.

The mass flow rate was: HF=0.2 kg/h, HFP=1.5 kg/h. Filter sinters (60 μm) were used as gas distribution system (4). The degree of conversion of the HFP was 99.999% and the purity of the heptafluoropropane obtained was 99.8%.

EXAMPLE 2

The process was performed as described in Example 1, the only difference being that the mass flow rate was doubled: HF=0.4 kg/h, HFP=3 kg/h.

The degree of conversion of the HFP and the purity of the heptafluoropropane were just as high as in Example 1.

EXAMPLE 3

The process was performed as described in Example 1, the only difference being that the mass flow rate was more than tripled: HF=0.65 kg/h, HFP=5 kg/h.

The degree of conversion of the HFP and the purity of the heptafluoropropane were just as high as in Example 1.

What is claimed is:

1. An improved process for the continuous preparation of 1,1,1,2,3,3,3-heptafluoropropane from HF and hexafluoropropene, allowing achievement of at least 99.99% conversion of the hexafluoropropene, wherein
   (a) HF and hexafluoropropene are converted in a first zone in the presence of at least one liquid hydrofluoride of an organonitrogen base corresponding to formula (I)

[B×nHF]   (I), in which B represents an organonitrogen base and n represents an integer or a fraction≦4, under a pressure of p1=1.3 to 10 bar,
   (b) the liquid reaction mixture obtained in (a) is transferred to a second zone under a pressure p2, in which p2≧1 bar and the pressure difference p1−p2≧0.3 bar,
   (c) the resulting heptafluoropropane is evaporated and isolated from the liquid reaction mixture, and
   (d) the remaining liquid reaction mixture is then transferred, after addition of hexafluoropropene and HF back into the first zone.

2. The process of claim 1, wherein [(CH$_3$)$_3$N×2.8 HF], [(C$_2$H$_5$)$_3$N×2.8 HF] or [(C$_4$H$_9$)$_3$N×2.6 HF] is used as hydrofluoride corresponding to formula (I).

3. The process of claim 1, wherein the conversion in the first zone is carried out at a temperature of 40 to 100° C.

4. The process of claim 1, wherein the conversion in the first zone is carried out at a pressure of $p_1$=1.5 to 5 bar.

5. The process of claim 1, wherein $p_1$ and $p_2$ are chosen such that the pressure difference $p_1-p_2$=0.3 bar to 2 bar.

6. The process of claim 1 wherein the first zone is a reactor and the second zone is a container.

7. The process of claim 1 wherein the degree of conversion of hexafluoropropene is at least 99.99%.

8. The process of claim 1, wherein the HFP is first dispersed in the catalyst via a gas distribution system in the form of small bubbles, which are characterized by rapid and complete dissolution.

9. The process of claim 8, wherein the HFP is introduced via the gas distribution system into the bottom region of the reactor and the presence of gas bubbles is limited to the bottom region of the reactor.

10. The process of claim 8, wherein the degree of conversion of hexaflouoropropene is at least 99.99%.

11. A process for the continuous preparation of 1,1,1,2,3,3,3-heptafluoropropane wherein
    (a) HF and hexafluoropropene are converted in a first zone in the presence of at least one liquid hydrofluoride of an organonitrogen base corresponding to formula (I)

[B×nHF]   (I), in which B represents an organonitrogen base and n represents an integer or a fraction≦4, under a pressure of p1=1.3 to 10 bar,
    (b) the liquid reaction mixture obtained in (a) is transferred to a second zone under a pressure p2, in which p2≧1 bar and the pressure difference p1−p2≧0.3 bar,
    (c) the resulting heptafluoropropane is evaporated and isolated from the liquid reaction mixture, and
    (d) the remaining liquid reaction mixture is then transferred, after addition of hexafluoropropene and HF back into the first zone,
    wherein conversion of hexafluoropropene is increased to at least 99.9% by passing the reaction mixture through said two zones.

* * * * *